United States Patent
Dreyfuss

(10) Patent No.: US 11,844,511 B2
(45) Date of Patent: Dec. 19, 2023

(54) SURGICAL SYSTEM AND METHOD PERMITTING PERCUTANEOUS INSERTION OF ANCHORS

(71) Applicant: ARTHREX, INC., Naples, FL (US)

(72) Inventor: Peter J. Dreyfuss, Naples, FL (US)

(73) Assignee: ARTHREX, INC., Naples, FL (US)

( * ) Notice: Subject to any disclaimer, the term of this patent is extended or adjusted under 35 U.S.C. 154(b) by 258 days.

(21) Appl. No.: 17/370,226

(22) Filed: Jul. 8, 2021

(65) Prior Publication Data
US 2023/0010055 A1 Jan. 12, 2023

(51) Int. Cl.
*A61B 17/04* (2006.01)
*A61B 17/34* (2006.01)

(52) U.S. Cl.
CPC ...... *A61B 17/0401* (2013.01); *A61B 17/3472* (2013.01); *A61B 2017/042* (2013.01); *A61B 2017/0409* (2013.01); *A61B 2017/0445* (2013.01); *A61B 2017/0464* (2013.01)

(58) Field of Classification Search
CPC ........ A61B 17/0401; A61B 2017/0409; A61B 17/3472; A61B 2017/0406; A61B 2017/0417; A61B 17/00234; A61B 17/34; A61B 2017/0445; A61B 2017/042; A61B 2017/0422; A61B 17/04; A61B 2017/0446; A61B 2017/0448; A61B 2017/0454; A61B 2017/0464; A61B 17/0469
See application file for complete search history.

(56) References Cited

U.S. PATENT DOCUMENTS

| | | |
|---|---|---|
| 3,111,945 A | 11/1963 | Von Solbrig |
| 3,469,573 A | 9/1969 | Florio |
| 4,008,912 A | 2/1977 | Kotov |
| 4,119,091 A | 10/1978 | Partridge |
| 4,146,022 A | 3/1979 | Johnson et al. |
| 4,606,335 A | 8/1986 | Wedeen |
| 4,643,178 A | 2/1987 | Nastari et al. |
| 4,667,662 A | 5/1987 | Titone et al. |

(Continued)

FOREIGN PATENT DOCUMENTS

WO 2015009808 A1 1/2015

OTHER PUBLICATIONS

International Preliminary Report on Patentability for International Application No. PCT/US2017/014924 dated Sep. 27, 2018.
(Continued)

*Primary Examiner* — Katherine M Shi
(74) *Attorney, Agent, or Firm* — Carlson, Gaskey & Olds, P.C.

(57) ABSTRACT

This disclosure details a surgical system and method, which is permits percutaneous insertion of anchors, and is useful in orthopedic surgical procedures involving fixation of soft tissue to bone. Because the anchors may be inserted percutaneously, the anchors can be inserted into bone without requiring a skin incision and without requiring a pre-drilled bone hole. As such, use of the disclosed system and method leads to a reduction in the number of steps in a surgical procedure, which reduces surgery time, while also reducing the size of openings formed in the skin relative to other known techniques, which reduces recovery times and results in smaller and less noticeable scarring.

19 Claims, 6 Drawing Sheets

(56) References Cited

U.S. PATENT DOCUMENTS

| | | |
|---|---|---|
| 5,012,818 A | 5/1991 | Joishy |
| 5,190,545 A | 3/1993 | Corsi et al. |
| 5,250,053 A | 10/1993 | Snyder |
| 5,318,566 A | 6/1994 | Miller |
| 5,415,658 A | 5/1995 | Kilpela et al. |
| 5,454,821 A | 10/1995 | Harm et al. |
| 5,462,542 A | 10/1995 | Alesi, Jr. |
| 5,501,688 A | 3/1996 | Whiteside et al. |
| 5,540,703 A | 7/1996 | Barker, Jr. et al. |
| 5,545,178 A | 8/1996 | Kensey et al. |
| 5,573,286 A | 11/1996 | Rogozinski |
| 5,573,542 A | 11/1996 | Stevens |
| 5,628,756 A | 5/1997 | Barker, Jr. et al. |
| 5,772,663 A | 6/1998 | Whiteside et al. |
| 5,788,697 A | 8/1998 | Kilpela et al. |
| 5,814,072 A | 9/1998 | Bonutti |
| 5,830,234 A | 11/1998 | Wojciechowicz et al. |
| 5,851,209 A | 12/1998 | Kummer et al. |
| 5,908,421 A | 6/1999 | Beger |
| 6,093,190 A | 7/2000 | Mattchen |
| 6,152,949 A | 11/2000 | Bonutti |
| 6,302,889 B1 | 10/2001 | Keller |
| 6,368,326 B1 | 4/2002 | Dakin et al. |
| 6,511,498 B1 | 1/2003 | Fumex |
| 6,610,071 B1 | 8/2003 | Cohn et al. |
| 6,716,234 B2 | 4/2004 | Grafton et al. |
| 6,942,684 B2 | 9/2005 | Bonutti |
| 6,955,683 B2 | 10/2005 | Bonutti |
| 7,207,090 B2 | 4/2007 | Mattchen |
| 7,207,993 B1 | 4/2007 | Baldwin et al. |
| 7,326,222 B2 | 2/2008 | Dreyfuss et al. |
| 8,162,997 B2 | 4/2012 | Struhl |
| 8,231,626 B2 | 7/2012 | Hulliger et al. |
| 8,298,247 B2 | 10/2012 | Sterrett et al. |
| 8,337,534 B2 | 12/2012 | Celli et al. |
| 8,460,295 B2 | 6/2013 | McClellan et al. |
| 8,574,235 B2 | 11/2013 | Stone |
| 8,672,969 B2 | 3/2014 | Stone et al. |
| 8,795,334 B2 | 8/2014 | Astorino et al. |
| 8,984,720 B2 | 3/2015 | Gephart |
| 9,216,036 B2 | 12/2015 | Johnstone |
| 9,545,251 B2 | 1/2017 | Bojarski et al. |
| 9,615,822 B2 | 4/2017 | Norton |
| 9,826,969 B2 | 11/2017 | Larsen |
| 9,888,997 B2 | 2/2018 | Dreyfuss et al. |
| 10,052,094 B2 | 8/2018 | Spenciner |
| 10,136,886 B2 | 11/2018 | Norton et al. |
| 10,143,506 B2 | 12/2018 | Dreyfuss et al. |
| 10,314,628 B2 | 6/2019 | Dooney et al. |
| 10,758,338 B2 | 9/2020 | Dreyfuss et al. |
| 2002/0095157 A1* | 7/2002 | Bowman ............ A61B 17/0401 606/75 |
| 2005/0033365 A1 | 2/2005 | Courage |
| 2009/0306668 A1 | 12/2009 | Dell'Oca |
| 2010/0211075 A1 | 8/2010 | Stone |
| 2010/0249853 A1 | 9/2010 | Celli et al. |
| 2012/0041454 A1* | 2/2012 | Johnstone ........ A61B 17/3472 606/139 |
| 2012/0109129 A1 | 5/2012 | Bernstein |
| 2013/0018375 A1 | 1/2013 | Dell'Oca |
| 2013/0096612 A1 | 4/2013 | Zajac et al. |
| 2013/0239974 A1 | 9/2013 | O'Brien et al. |
| 2014/0249530 A1 | 9/2014 | Babikian et al. |
| 2014/0257377 A1 | 9/2014 | Akutsu et al. |
| 2015/0127003 A1 | 5/2015 | Songer et al. |
| 2015/0173754 A1* | 6/2015 | Norton ............... A61B 17/0401 606/228 |
| 2016/0183991 A1 | 6/2016 | Pratt |
| 2017/0265917 A1 | 9/2017 | Dreyfuss et al. |
| 2017/0265918 A1 | 9/2017 | Dooney et al. |

OTHER PUBLICATIONS

Y.M. Por, M.J. Lavin, "Techniques of intraocular lens suspension in the absence of capsular/zonular support", Survey of Ophthalmology, vol. 50, nr. 5, Sep.-Oct. 2005.
Arthrex Inc. "SoftStitch Meniscal Repair System. Surgical Techniques." 2019.
Arthrex Inc. "Shoulder an Elbow. Next generation in repair and reconstruction." pp. 1-100. 2020.
Smith & Nephew, "Q-Fix All-suture Implants," Copyright 2015 Smith & Nephew, Inc. Trademark of Smtih & Nephew. Reg. US Pat & TM Office. P/N A1141 Rev. B Jan. 2015.
Lawhorn, Keith, M.D. MaxFire MarXmen Meniscal Repair Device, Biomet Sports Medicine, Form No. BSM0211, Rev. 11509.
Arthrex Inc. "FiberStitch all-inside Meniscal Repair. Surgical Technique." 2019.
Arthrex Inc. "FiberTak Bicept Implant System. Biceps Tendonesis Surgical Technique." 2019.

* cited by examiner

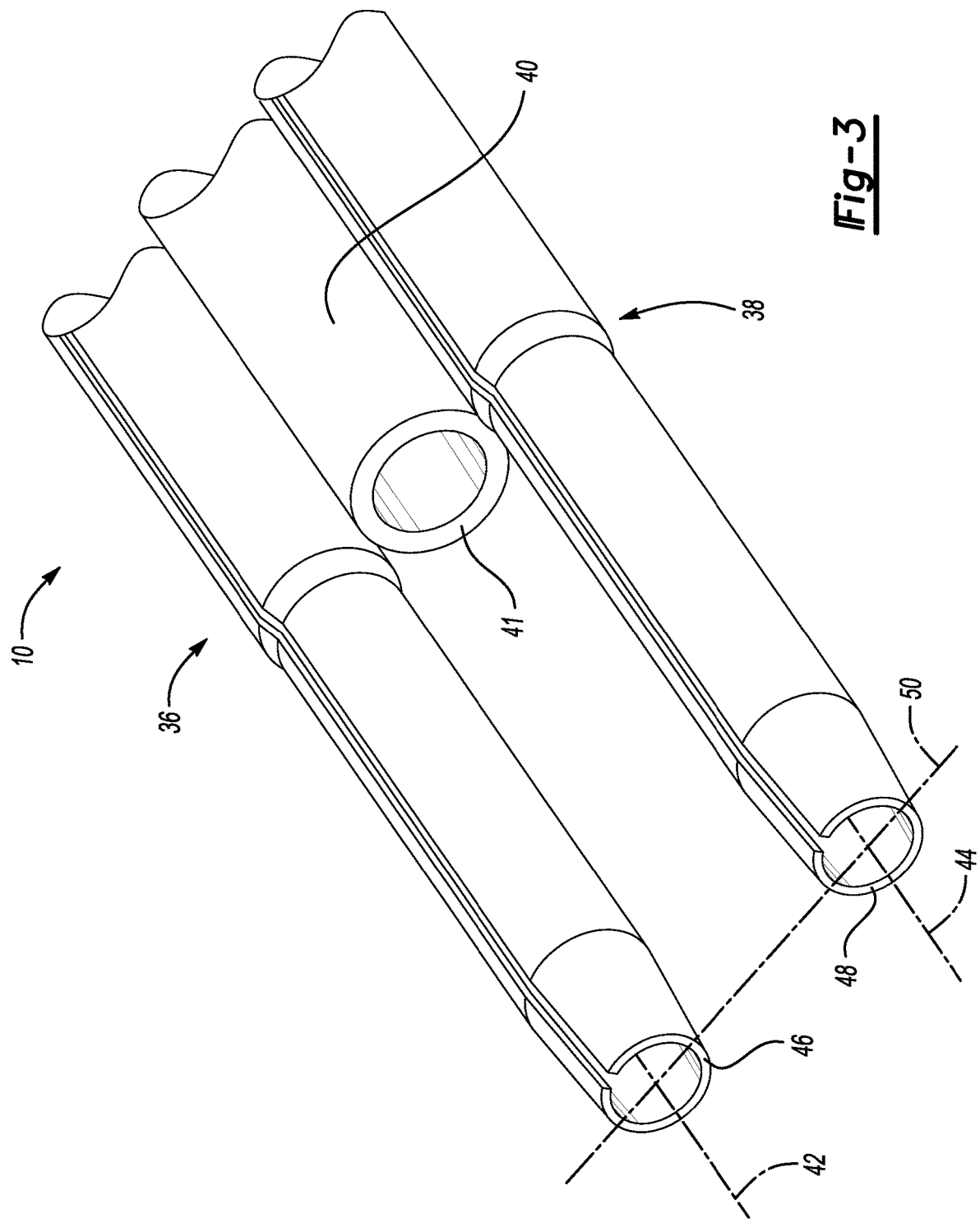

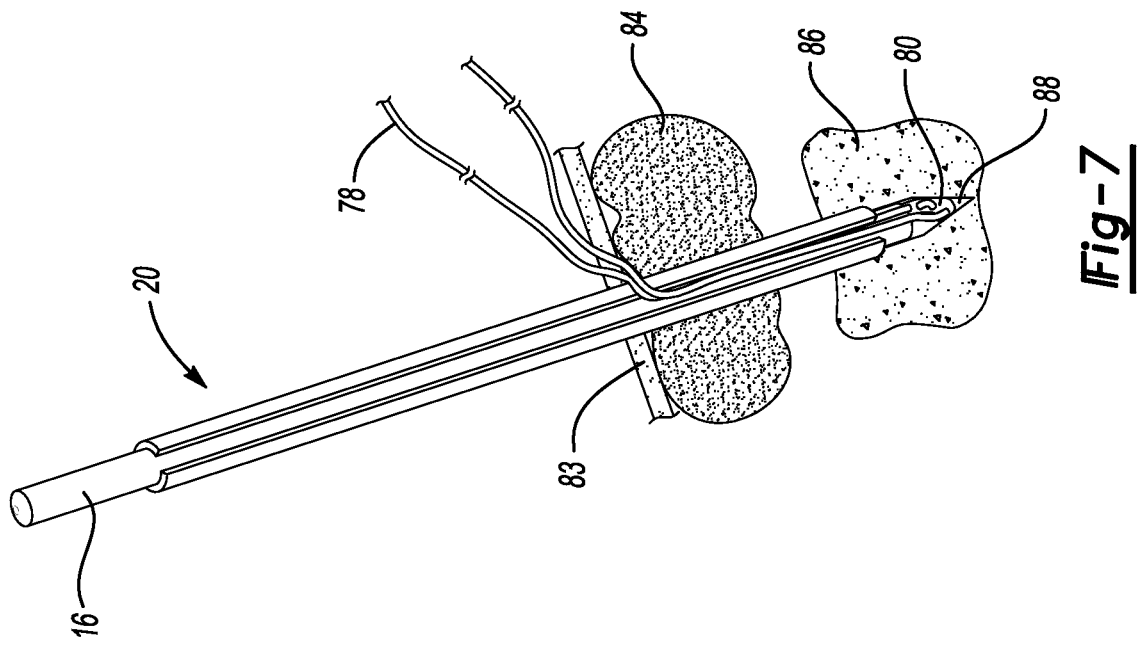
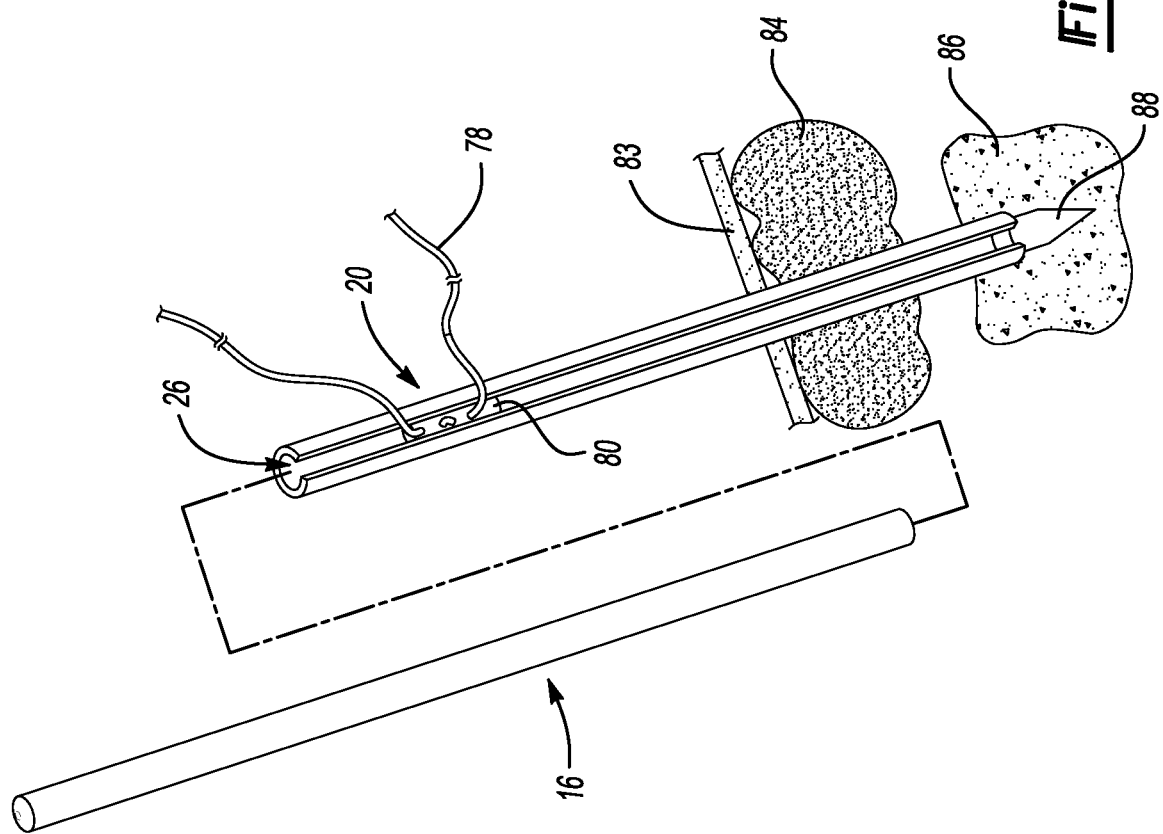

SURGICAL SYSTEM AND METHOD PERMITTING PERCUTANEOUS INSERTION OF ANCHORS

BACKGROUND

This disclosure relates to a surgical system and method permitting percutaneous insertion of anchors to facilitate reattachment of soft tissue to bone and, in turn, to promote healing of the damaged soft tissue and the corresponding joint(s).

When soft tissue such as a ligament or a tendon becomes detached from a bone, surgery is usually required to reattach or reconstruct the tissue. In such surgeries, which may be performed arthroscopically, one or more small skin incisions are usually required in order to access an area within a patient's body, such as a joint space, where the surgery is performed.

SUMMARY

This disclosure details a surgical system and method, which is permits percutaneous insertion of anchors, and is useful in orthopedic surgical procedures involving fixation of soft tissue to bone. Because the anchors may be inserted percutaneously, the anchors can be inserted into bone without requiring a skin incision and without requiring a pre-drilled bone hole.

The disclosed system includes a guide which is cannulated and includes a slot along its entire length. In a disclosed technique, a trocar is inserted into the cannulation. Together, the guide and trocar are pushed through the skin, through soft tissue, and into bone to form a bone hole. Then, the trocar is removed from the guide while leaving the guide partially in the bone hole. Next, a pusher is used to push an anchor through the guide into the bone hole. The anchor is a deformable, tubular sheath and may be part of a construct including a strand of suture. The construct may include additional anchors. The trocar, guide, and rod may be used to insert additional anchors adjacent the first anchor, as many times as desired, to secure the soft tissue to bone.

A system according to the present disclosure includes, among other things, a guide including a tube exhibiting a length between a distal end and a proximal end. The tube includes a through-bore extending from the distal end of the tube to the proximal end of the tube, and the tube includes a slot extending from the distal end of the tube to the proximal end of the tube. Further, the system includes a trocar including a shaft and a distal end section tapering to provide a sharp tip at a distal end of the trocar. The trocar is selectively insertable into the tube and removable from the tube, and, when the trocar is fully inserted into the tube, the sharp tip projects distally of the distal end of the tube. The system also includes a pusher selectively insertable into the tube and removable from the tube, and an anchor. The anchor is a deformable sheath and is insertable into bone by being pushed through the tube by the pusher.

A method according to the present disclosure includes advancing a trocar and a tube through skin, through soft tissue, and into bone to form a bone hole. During the advancing step, the trocar is arranged within a through-hole of the tube such that a sharpened tip of the trocar projects distally of a distal end of the tube. Further, the method includes removing the trocar from the tube while leaving a portion of the tube in the bone hole, and using a pusher to push the anchor into the bone hole through the through-hole.

BRIEF DESCRIPTION OF THE DRAWINGS

In FIG. 2, the trocar and guide are arranged side-by-side.

FIG. 3 is a perspective view of a portion of another example guide.

FIG. 6 illustrates a step of the example method, and in particular illustrates an anchor arranged in the guide.

FIG. 7 illustrates a step of the example method, and in particular illustrates an anchor being inserted into to the bone hole by being pushed out of the guide by a pusher.

DETAILED DESCRIPTION

Figure 1:
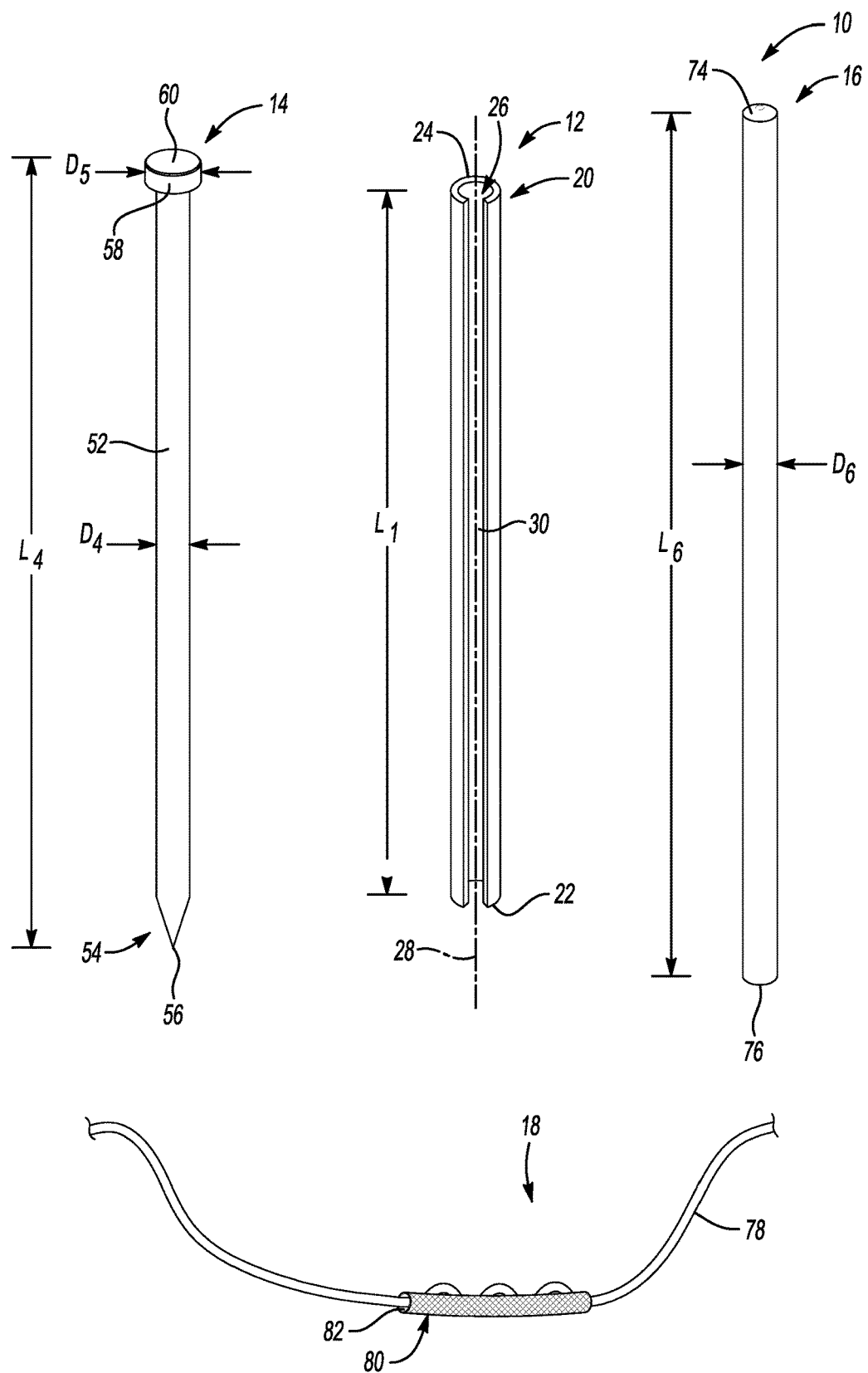
FIG. 1 illustrates an example surgical system according to this disclosure.

This disclosure details a surgical system and method, which permits percutaneous insertion of anchors, and is useful in orthopedic surgical procedures involving fixation of soft tissue to bone. FIG. 1 illustrates an example system 10. The system 10 includes a guide 12, a trocar 14, a pusher 16, and a construct 18. Each of the components will now be described in more detail. While four components are shown, the system 10 may include additional or fewer components.

In FIG. 1, the guide 12 includes a tube 20 exhibiting a length $L_1$ between a distal end 22 and a proximal end 24. The tube 20 includes a through-bore 26 extending from the distal end 22 to the proximal end 24. The through-bore 26 may be referred to as a cannula or cannulation. The through-bore 26 is a hole, which is circular in cross-section, and is centered along a central axis 28 of the tube 20. Further, the tube 20 includes a slot 30 extending along the entire length of the tube 20, from the distal end 22 to the proximal end 24. Both the through-bore 26 and the slot 30 exhibit the length $L_1$. The slot 30 is a circumferential gap in a wall of the tube 20. The slot 30 extends radially from an exterior surface of the tube 20 to the through-bore 26. The slot 30 provides access to and from the through-bore 26 via the slot 30. In this example, the width of the slot 30 is constant along the entire length of the tube 20.

Figure 2:
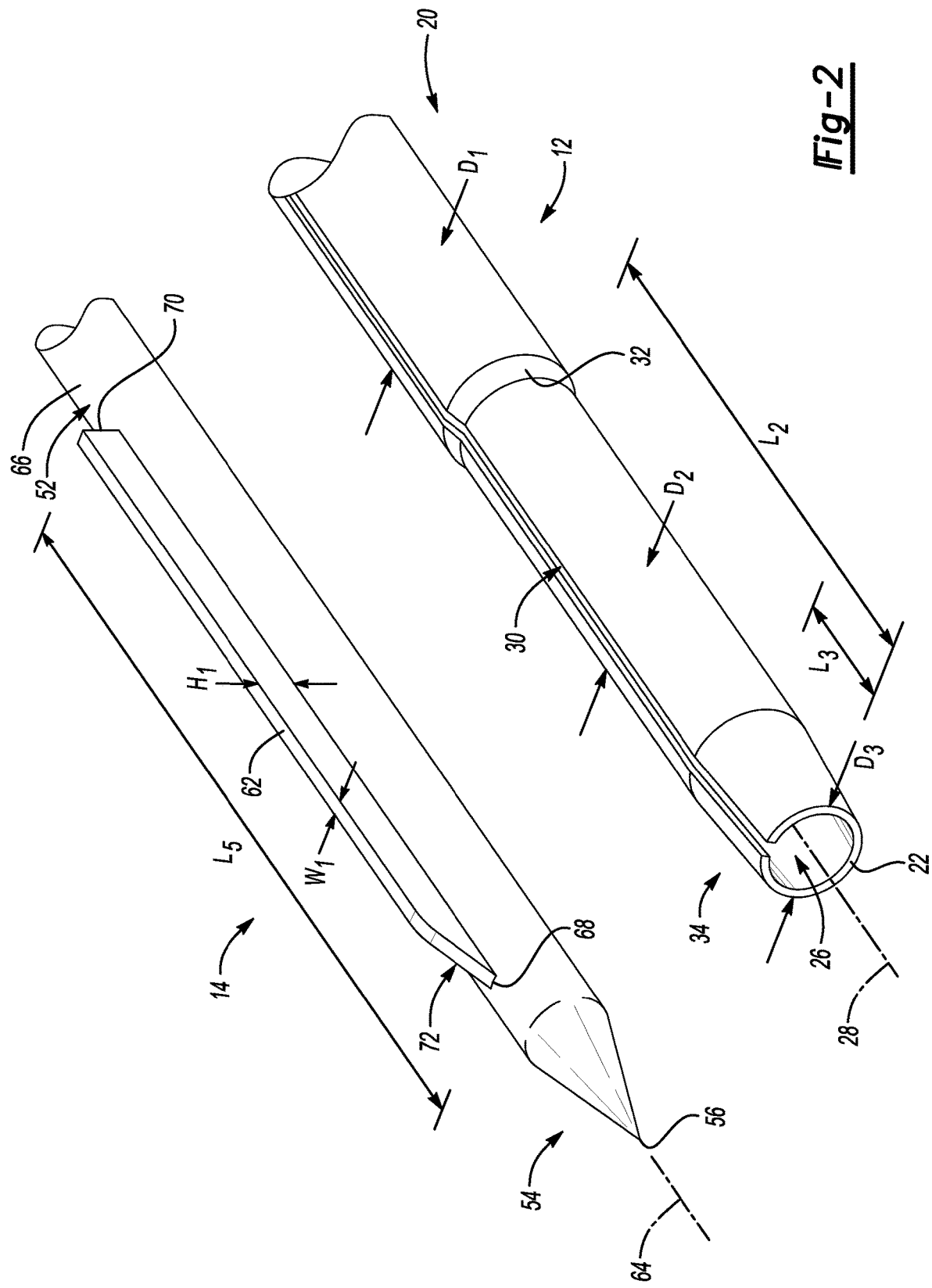
FIG. 2 is a perspective view of a portion of an example trocar and a portion of an example guide.

With joint reference to FIGS. 1 and 2, the tube 20 exhibits an outer diameter $D_1$ along a majority of the length $L_1$. Adjacent the distal end 22, however, the tube 20 exhibits a variable outer diameter to facilitate interaction with, and specifically penetration of, skin, soft tissue, and bone. With reference to FIG. 2, at a point spaced-apart proximal from the distal end 22 by a length $L_2$, the tube 20 exhibits a shoulder 32. At or adjacent the shoulder 32, the outer diameter of the tube 20 reduces from outer diameter $D_1$ to outer diameter $D_2$, which is less than $D_1$. The shoulder 32 may be provided by a surface normal to the central axis 28 or inclined relative to the central axis 28. Moving distally from the shoulder 32, the tube 20 exhibits the outer diameter $D_2$. Approaching the distal end 22, the outer diameter reduces even further in this example. In particular, at a point spaced-apart proximally from the distal end 22 by a length $L_3$ which is less than $L_2$, the tube 20 exhibits a tapered section 34 throughout which the outer diameter of the tube 20 gradually reduces from $D_2$ to a lesser outer diameter $D_3$ at the distal end 22. The outer diameter of the tube 20 exhibits a constant taper angle throughout the tapered section 34.

In the example of FIGS. 1 and 2, the guide 12 includes a single tube 20. However, in or embodiments, the guide 12 may include additional tubes. As an example, in FIG. 3, the guide 12 includes a first tube 36 and a second tube 38. In this embodiment, the first and second tubes 36, 38 are configured substantially the same as the tube 20. The guide 12 is also arranged such that the first and second tubes 36, 38 are arranged parallel to one another and such that the distal ends are aligned. Specifically, the guide 12 of FIG. 3 includes a central support 40. The central support 40, in this example, is a cylindrical structure which extends along a portion of the first and second tubes 36, 38. A distal end 41 of the central support 40 is proximal of shoulders of the first and second tubes 36, 38. The first and second tubes 36, 38 are attached to opposite sides of central support 40 such that respective central axes 42, 44 of the first and second tubes 36, 38 are parallel to one another and such that respective distal ends 46, 48 are aligned with one another. Regarding the alignment of the distal ends 46, 48, the distal ends 46, 48 both lie on a plane 50 which is perpendicular to the axes 42, 44. The first and second tubes 36, 38 are spaced-apart from one another in a direction perpendicular to the axes 42, 44 by the width of the central support 40, which in this example is equal to the outer diameter $D_1$. The central support 40 could have a greater or lesser width, however. In this example, the first and second tubes 36, 38 and the central support 40 are formed as separate structures and are connected together by welding, for example. It should be understood, however, that a one-piece, seamless structure could provide the first and second tubes 36, 38 and central support 40. While embodiments are disclosed in which guides include one and two tubes, respectively, the guide may include additional tubes.

With reference back to FIG. 1, the trocar 14 is selectively insertable into and removable from the tube 20. The trocar 14 is configured to penetrate skin, soft tissue, and bone. In this example, the trocar 14 includes a shaft 52 and a distal end section 54 tapering to provide a sharp tip at a distal end 56 of the trocar 14. Further, in this example, the trocar 14 exhibits a head 58 attached to a proximal end of the shaft 52. The head 58 provides a proximal end 60 of the trocar 14, in this example. The trocar 14 exhibits a length $L_4$ between the proximal end 60 and the distal end 56. The length $L_4$ is greater than the length $L_1$ of the tube 20 such that, when the trocar 14 is fully inserted into the tube 20, the distal end section 54 at least partially projects distally of the distal end 22 of the tube 20 such that the distal end section 54 can penetrate skin, soft tissue, and bone.

The shaft 52 is cylindrical and exhibits an outer diameter $D_4$ substantially equal to, but slightly less than, a diameter of the through-bore 26, such that the shaft 52 is close-fitting relative to the through-bore 26 while still being readily movable within the through-bore 26. The distal end section 54 exhibits a constant taper angle, in this example, and gradually reduces from the outer diameter $D_4$ moving distally toward the distal end 56. The head 58 exhibits an outer diameter $D_5$ greater than the outer diameter $D_4$. The head 58 is sized such that the head 58 is not insertable into the through-bore 26. Specifically, the head 58 is configured such that contact between the head 58 and the proximal end 24 of the tube 20 prevents further distal movement of the trocar 14 into the tube 20. The head 58 may be configured to include a grip or handle. The head 58 may also include a surface, such as a flat surface, conducive to being struck by a tool such as a hammer or mallet. The head 58 is not required in all examples.

Figure 4:
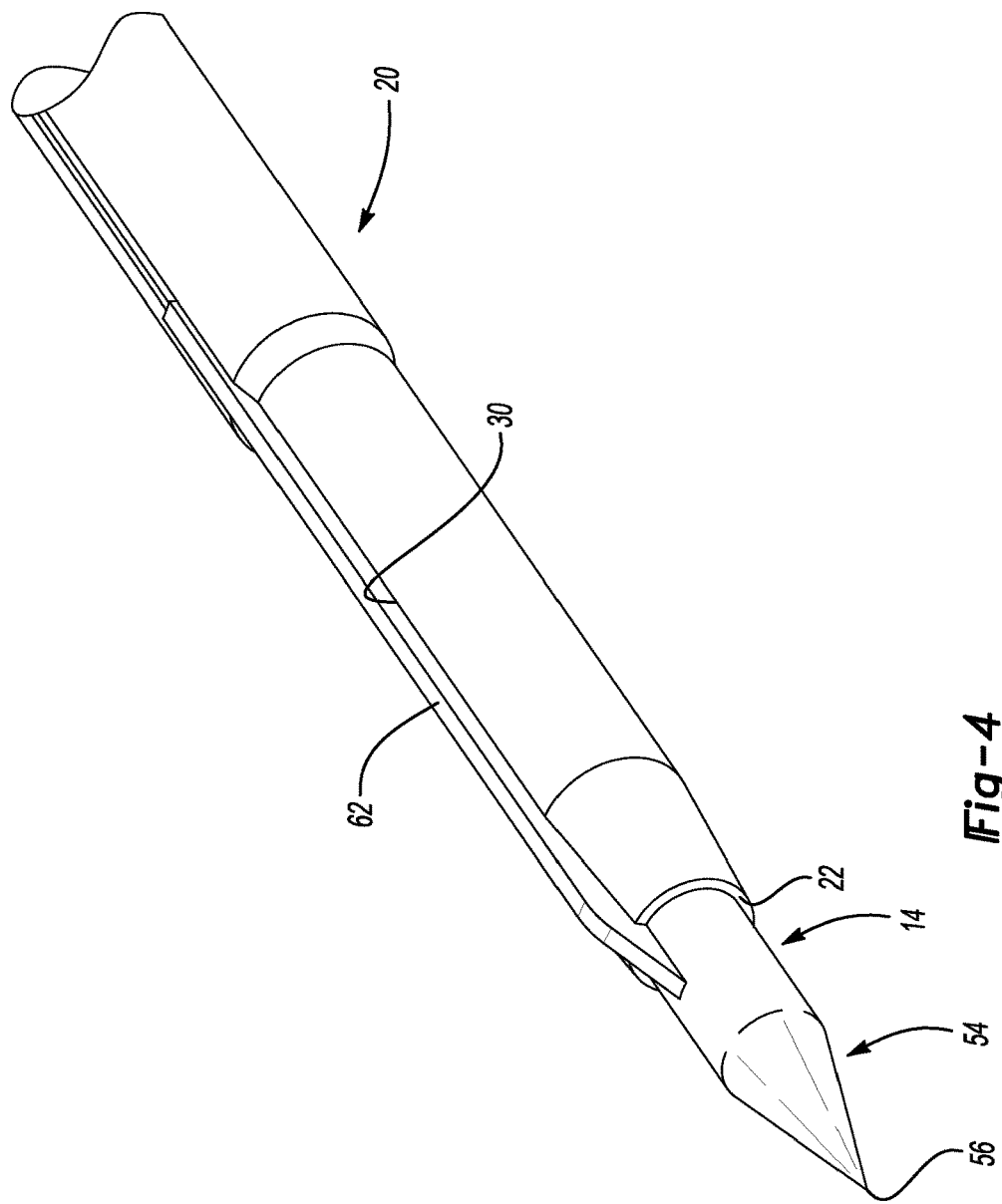
FIG. 4 is a perspective view of the trocar of FIG. 2 inserted into the guide of FIG. 2.

With reference to FIG. 2, in an example, the trocar 14 includes a rib 62. The rib 62 projects radially, in a direction perpendicular to a central axis 64 of the trocar 14, from an outer surface 66 of the trocar 14. The rib 62 exhibits a height $H_1$ in the radial direction such that, when the trocar 14 is inserted into the tube 20, the rib 62 projects partially radially outward of the slot 30, as generally shown in FIG. 4. A width $W_1$ of the rib 62 is substantially equal to, but slightly less than the slot 30 such that the rib 62 can fit into the slot 30 and, when the rib 62 is in the slot 30, the rib 62 substantially prevents rotation of the trocar 14 relative to the tube 20. Further, the rib 62 substantially fills the slot 30 such that skin, soft tissue, and bone are prevented from entering the slot 30 when the trocar 14 is fully inserted into the tube 20.

The rib 62, in this example, exhibits a constant height $H_1$ along a majority of its length $L_5$, which extends between a distal end 68 and a proximal end 70 of the rib 62. At a distal end section 72 adjacent the distal end 68 of the rib 62, the height of the rib 62 gradually diminishes such that, at the distal end 68, the height of the rib 62 blends into the outer surface 66. The distal end section 72 exhibits a constant angle along its length, in an example. The distal end section 72 effectively provides the rib 62 with a sloped leading edge which facilitates insertion of the trocar 14 into skin, soft tissue, and bone, and also directs skin, soft tissue, and bone away from the slot 30.

With reference back to FIG. 1, the pusher 16 is a rod configured to push and slide a portion of the construct 18, such as an anchor, sleeve, or implant, along the tube 20 and into a bone hole. The pusher 16 is selectively insertable into and removable from the tube 20. In this example, the pusher 16 is configured as a cylindrical shaft having a diameter $D_6$ and length $L_6$ between proximal and distal ends 74, 76. The length $L_6$ is greater than the length $L_1$ in an example. The diameter $D_6$ is such that the pusher 16 is able to slide within the through-bore 26. In an example, the diameter $D_6$ is equal to the diameter $D_4$. While not shown, the pusher 16 may include a grip or handle adjacent the proximal end 74.

The construct 18 includes at least one anchor and at least one strand of suture. In the example of FIG. 1, the construct 18 includes a strand of suture 78 and an anchor 80. The strand of suture 78 is a high strength braided suture, such as Arthrex, Inc.'s FiberTape®. The strand of suture 78 may include a multifilament cover formed of a plurality of braided fibers of ultrahigh molecular weight polyethylene (UHMWPE) and fibers of polyester. The cover may surround a core formed of twisted fibers of ultrahigh molecular weight polyethylene (UHMWPE). Other types of suture come within the scope of this disclosure, however.

The anchor 80, in this example, is a deformable sheath. While one anchor 80 is shown, the construct 18 may include additional sheaths arranged relative to the strand of suture 78. The anchor 80 has a tubular body that is free of barbs and includes a through-bore 82 accommodating the strand of suture 78. The strand of suture 78 is flexible and is passed through the through-bore 82 of the sheath. The strand of suture 78 is encased by the sheath throughout substantially the entire length of the sheath, with the exception of a plurality of splice points. The anchor includes at least one splice point, in which the strand of suture 78 exits and re-enters the through-bore 82. In this example, the sheath includes six splice points. The strand of suture 78 either exits or re-enters the through-bore 82 through each of the splice points.

The arrangement of the strand of suture 78 relative to the anchor 80 is such that applying tension to the strand of suture 78 causes the anchor 80 to essentially bunch together into a configuration in which the anchor 80 lodges itself in bone and resists applied forces such that a surgeon can use the strand of suture 78 to fix soft tissue to bone to promote healing.

The construct 18 may be referred to as a "soft" construct because it is formed of soft materials such as yarns, fibers, filaments, strings, fibrils, strands, sutures, etc., or any combination of such materials. The soft materials may be synthetic or natural materials, or combinations of synthetic and natural materials, and may be biodegradable or non-biodegradable within the scope of this disclosure. In an embodiment, the construct 18 is made exclusively of soft, suture-based materials. The soft materials confer the ability to be inserted into or through tissue (e.g., bone, ligament, tendon, cartilage, etc.) and then bunch together, collapse, expand, and/or change shape to fixate the construct 18 relative to the tissue.

An example method of using the system 10 to fix soft tissue to bone will now be described. A surgeon may perform the method either partially or entirely. One or more steps of the method may be performed by a surgical assistant. The method may be performed either partially or entirely during a surgical procedure.

Figure 5:
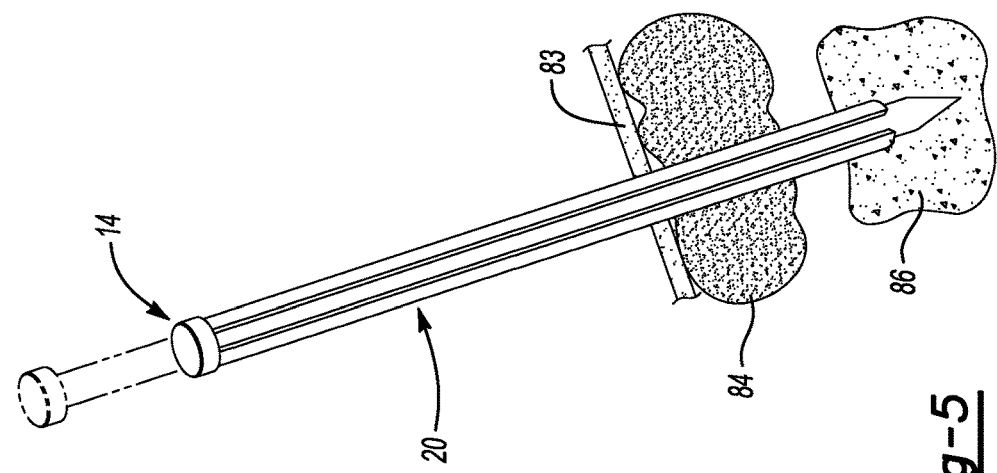
FIG. 5 illustrates a step of an example method, and in particular illustrates a trocar and guide inserted through skin, through soft tissue, and into bone to form a bone hole.

In the method, the trocar 14 is first fully inserted into the tube 20, as substantially shown in FIG. 4. With reference to FIG. 5, the trocar 14 and tube 20 are then moved together such that the trocar 14 penetrates skin 83, soft tissue 84, and bone 86. The soft tissue 84 may be a tendon or ligament, as examples. The bone 86 may be a bone adjacent the shoulder or knee, as examples. In particular, with reference to FIG. 5, the trocar 14 and tube 20 extend through the entirety of the thickness of skin 83 and soft tissue 84. Further, the trocar 14 penetrates a cortical layer of the bone 86 and extends into the cancellous layer of the bone 86 to form a bone hole 88 (FIG. 6). The tube 20 also partially projects into the bone 86.

A force from a tool may be applied to a proximal end of the trocar 14 and/or tube 20 to facilitate penetration of bone. In an example, the shoulder 32 acts as a depth limiter and abuts, but does not penetrate, the skin 83.

Once the bone hole 88 is formed, the trocar 14 is removed from the tube 20, while the tube 20 remains in bone 86. With the trocar 14 removed, the anchor 80 is inserted into the through-bore 26 of the tube 20, as shown in FIG. 6. With the anchor 80 in the through-bore 26, the strand of suture 78 extends out of the tube 20 through the slot 30 such that the strand of suture 78 is accessible by a surgeon. The pusher 16 is used to push the anchor 80 into the bone hole 88. Specifically, the pusher 16 is inserted into the through-bore 26, and the surgeon pushes the distal end 78 of the pusher 16 against a proximal end of the anchor 80 until the anchor 80 reaches the bone hole 88, as shown in FIG. 7. The anchor 80 is not folded as it passes through the tube 20. When the anchor 80 reaches the bone hole, the surgeon tensions the strand of suture 78 to deform the anchor 80 in a manner such that the anchor 80 lodges itself in bone 86.

Figure 9:
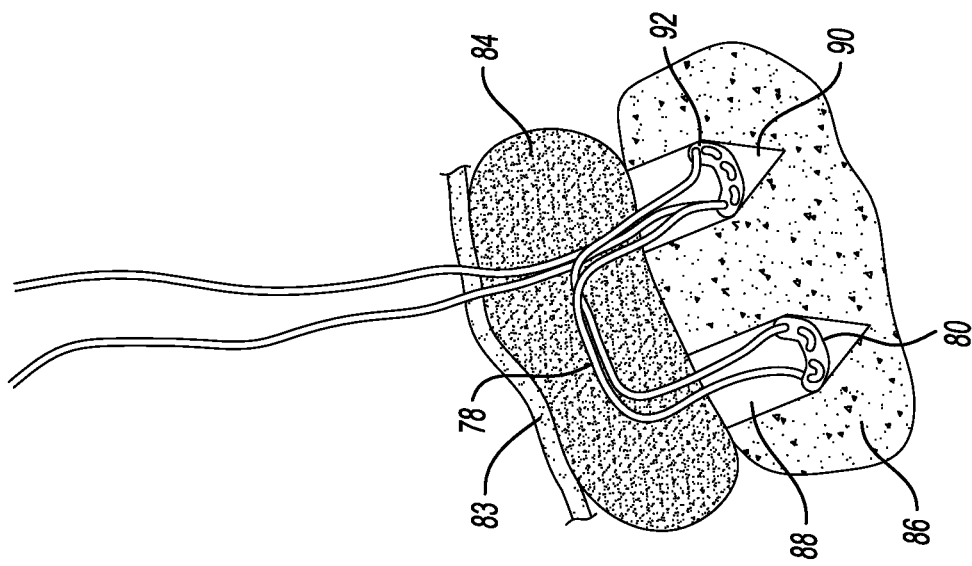
FIG. 9 illustrates a step of the example method, and in particular illustrates a construct including two anchors arranged in respective bone holes, and suture holding soft tissue in place relative to bone.
Figure 8:
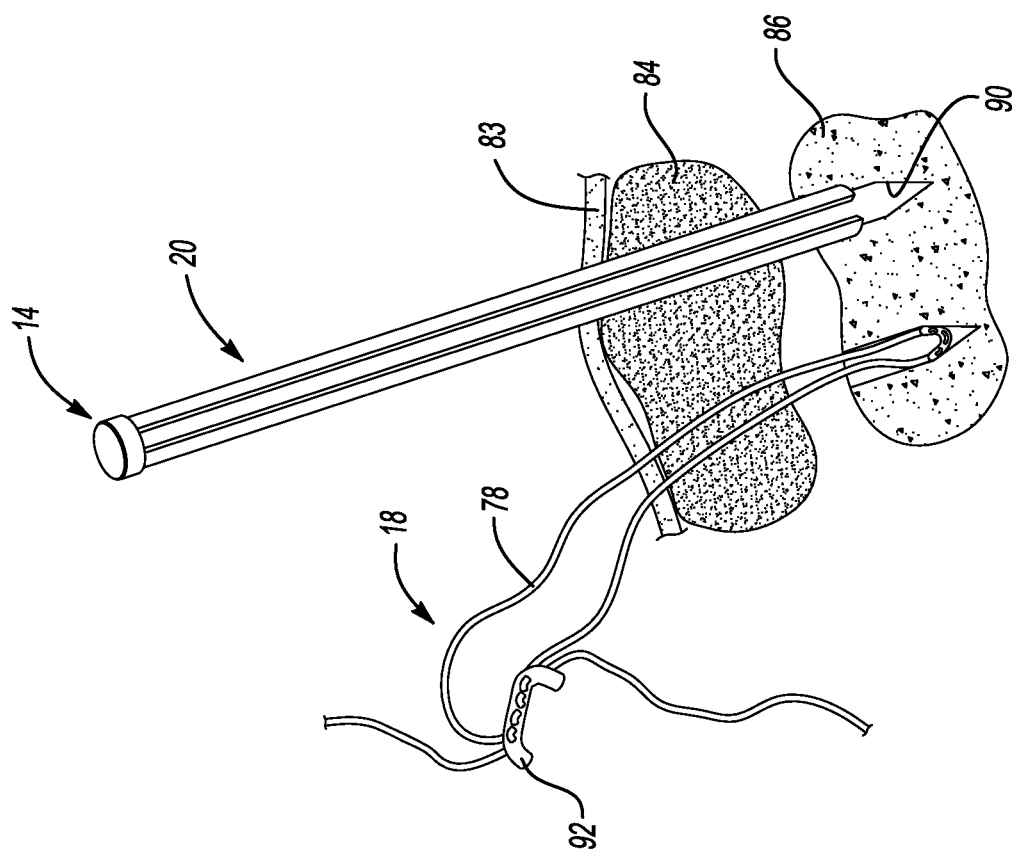
FIG. 8 illustrates a step of the example method, and in particular illustrates a first anchor arranged in a bone hole, and, adjacent the first anchor, a trocar and guide inserted through the skin, through the soft tissue, and into bone to form another bone hole.

As generally shown in FIG. 8, the steps of FIGS. 5-7 may be repeated to insert additional anchors into the bone 86. In FIG. 8, for example, the tube 20 has been removed from bone 86, and the trocar 14, or a similar trocar, has been re-inserted into the tube 20. Together, the trocar 14 and tube 20 have again penetrated the skin 83, soft tissue 84, and bone 86 to form another bone hole 90 spaced-apart from the bone hole 88. The bone hole 90 is sized and shaped substantially the same as bone hole 88. Further, in the example of FIG. 8, another anchor 92 similar to anchor 80 is included in the construct 18. The trocar 14 is removed from the tube 20 and the anchor 92 is inserted into the tube 20 and, using the pusher 16, is pushed into the bone hole 90. Tension is then applied to the strand of suture 78 to deform the anchor 92 and lodge it in place, as generally shown in FIG. 9. As shown in FIG. 9, a surgeon has tensioned the strand of suture 78 such that it holds the soft tissue 84 in place relative to bone 86. The surgeon may tie the strand of suture 78 into one or more knots to fix the soft tissue 84 in place.

While two anchors have been inserted in FIG. 9, the surgeon may insert one or more anchors, including three or more anchors, as desired. Further, while the same tube 20 is used to insert both anchors 80, 92, it should be understood that the guide 12 of FIG. 3 could be used to insert the anchors 80, 92. In that example, two trocars are arranged into the two tubes 36, 38 to form two bone holes essentially simultaneously.

The system 10 is used to percutaneously insert anchors into bone. The system 10 does not require one to first create an incision in the skin 83, nor does the system 10 require one to pre-drill a bone hole. Rather, together with the tube 20, the trocar 14 facilitates piercing of skin 83 and formation of a bone hole in a single inserting step. Thus, the system 10 reduces the number of steps in a surgical procedure, which reduces surgery time, while also reducing the size of openings formed in the skin 83 relative to other known techniques, which reduces recovery times and results in smaller and less noticeable scarring.

It should be understood that directional terms such as distal, proximal, etc., are used herein consistent with their art-accepted meaning. Additionally, directional terms such as axial, radial, and circumferential are used according to their art-accepted meaning. These terms should not otherwise be considered limiting.

Although the different examples have the specific components shown in the illustrations, embodiments of this disclosure are not limited to those particular combinations. It is possible to use some of the components or features from one of the examples in combination with features or components from another one of the examples. In addition, the various figures accompanying this disclosure are not necessarily to scale, and some features may be exaggerated or minimized to show certain details of a particular component or arrangement.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:
1. A system, comprising:
  a guide including a tube exhibiting a length between a distal end and a proximal end, wherein the tube includes a through-bore extending from the distal end of the tube to the proximal end of the tube, and wherein the tube includes a slot extending from the distal end of the tube to the proximal end of the tube;

a trocar including a shaft and a distal end section, wherein an entirety of the distal end section tapers at a constant taper angle to provide a sharp tip at a distal end of the trocar, wherein the trocar is selectively insertable into the tube and removable from the tube, wherein, when the trocar is fully inserted into the tube, the sharp tip projects distally of the distal end of the tube;

a pusher selectively insertable into the tube and removable from the tube; and an anchor, wherein the anchor is a deformable sheath and is insertable into bone by being pushed through the tube by the pusher.

2. The system as recited in claim 1, wherein the trocar includes a rib projecting radially into the slot.

3. The system as recited in claim 2, wherein a portion of the rib at least partially projects radially through the slot.

4. The system as recited in claim 3, wherein a radial dimension of the rib gradually reduces adjacent a distal end of the rib.

5. The system as recited in claim 1, wherein an outer diameter of the tube is tapered adjacent the distal end of the tube.

6. The system as recited in claim 1, wherein:
the anchor is part of a construct,
the construct includes a strand of suture, and
when the anchor is within the through-bore of the tube, the strand of suture at least partially projects out of the slot.

7. The system as recited in claim 6, wherein:
the strand of suture is arranged relative to the anchor such that application of tension to the strand of suture deforms the anchor.

8. The system as recited in claim 7, wherein the anchor is free of barbs.

9. The system as recited in claim 6, wherein the anchor is a first anchor and the construct includes a second anchor.

10. The system as recited in claim 9, wherein the first and second anchors each include at least one splice point in which the strand of suture exits and re-enters a through bore of a respective one of the first and second anchors.

11. The system as recited in claim 1, wherein the tube exhibits a shoulder such that, distal of the shoulder, an outer diameter of the tube is reduced relative to an outer diameter of the tube proximal of the shoulder.

12. The system as recited in claim 1, wherein a length of the trocar is greater than a length of the tube.

13. The system as recited in claim 1, wherein the distal end section is conical.

14. A system, comprising:
a guide including a tube exhibiting a length between a distal end and a proximal end, wherein the tube includes a through-bore extending from the distal end of the tube to the proximal end of the tube, and wherein the tube includes a slot extending from the distal end of the tube to the proximal end of the tube;

a trocar including a shaft and a distal end section tapering to provide a sharp tip at a distal end of the trocar, wherein the trocar is selectively insertable into the tube and removable from the tube, wherein, when the trocar is fully inserted into the tube, the sharp tip projects distally of the distal end of the tube;

a pusher selectively insertable into the tube and removable from the tube; and an anchor, wherein the anchor is a deformable sheath and is insertable into bone by being pushed through the tube by the pusher, wherein the tube is a first tube, and wherein the guide includes a second tube attached to and spaced-apart from the first tube in a direction normal to central axes of the first and second tubes.

15. The system as recited in claim 14, wherein:
the second tube includes a through-bore extending from a distal end of the second tube to a proximal end of the second tube, and
the second tube includes a slot extending from the distal end of the second tube to the proximal end of the second tube.

16. The system as recited in claim 14, wherein:
the first and second tubes each exhibit a shoulder such that, distal of the shoulder, an outer diameter of the respective first and second tube is reduced relative to an outer diameter proximal of the shoulder,
the guide includes a central support attached to the first tube and the second tube, and
a distal end of the central support is proximal of the shoulders of the first and second tubes.

17. The system as recited in claim 16, wherein the central support is a cylindrical structure.

18. The system as recited in claim 16, wherein the guide is configured such that central axes of the first and second tubes are parallel to one another.

19. The system as recited in claim 18, wherein the guide is configured such that distal ends of the first and second tubes lie on a common plane perpendicular to the central axes.

* * * * *